(12) United States Patent
Mainz

(10) Patent No.: US 10,850,026 B2
(45) Date of Patent: Dec. 1, 2020

(54) PERISTALTIC PUMP OF AN INFUSION SYSTEM FOR DELIVERY OF SMALL VOLUMES OF FLUID

(71) Applicant: CareFusion 303, Inc., San Diego, CA (US)

(72) Inventor: Gabriel Mainz, San Diego, CA (US)

(73) Assignee: CareFusion Corporation, San Diego, CA (US)

( * ) Notice: Subject to any disclaimer, the term of this patent is extended or adjusted under 35 U.S.C. 154(b) by 165 days.

(21) Appl. No.: 15/974,459

(22) Filed: May 8, 2018

(65) Prior Publication Data

US 2019/0344011 A1 Nov. 14, 2019

(51) Int. Cl.
| | |
|---|---|
| *A61M 5/14* | (2006.01) |
| *A61M 5/142* | (2006.01) |
| *A61M 39/08* | (2006.01) |
| *A61M 39/22* | (2006.01) |

(52) U.S. Cl.
CPC ........ *A61M 5/14228* (2013.01); *A61M 39/08* (2013.01); *A61M 39/22* (2013.01); *A61M 2205/07* (2013.01); *A61M 2205/106* (2013.01)

(58) Field of Classification Search
CPC .. A61M 5/14228; A61M 39/08; A61M 39/22; A61M 2205/07; A61M 2205/106; A61M 2005/14513; A61M 5/14224; F04B 43/12; F04B 43/1223
See application file for complete search history.

(56) References Cited

U.S. PATENT DOCUMENTS

| | | | |
|---|---|---|---|
| 4,014,318 A * | 3/1977 | Dockunn | A61M 1/1053 600/16 |
| 2003/0073952 A1 | 4/2003 | Flaherty et al. | |
| 2012/0157919 A1* | 6/2012 | Butterfield | A61M 5/142 604/151 |
| 2014/0103071 A1* | 4/2014 | Park | A45D 34/00 222/207 |
| 2015/0328399 A1 | 11/2015 | Heitmeier et al. | |
| 2017/0218945 A1 | 8/2017 | Rotem et al. | |

FOREIGN PATENT DOCUMENTS

| | | |
|---|---|---|
| CN | 1373294 A | 10/2002 |
| DE | 19818646 A1 | 10/1999 |

* cited by examiner

*Primary Examiner* — Bhisma Mehta
*Assistant Examiner* — Daniel Moore
(74) *Attorney, Agent, or Firm* — Mintz Levin Cohn Ferris Glovsky and Popeo, P.C.

(57) ABSTRACT

A medical fluid infusion system includes a peristaltic pump system configured to deliver a fluid drug to a patient. The peristaltic pump system can include a peristaltic pump in communication with a pressure source. In some embodiments, the peristaltic pump system can include a valve body positioned between the peristaltic pump and pressure source for controlling the delivery of pressurized fluid (e.g., air, liquid) to the peristaltic pump. The peristaltic pump can include more than one occluder, with each occluder having a flexible member that can form a collapsed and extended configuration based on a pressure provided to the flexible member.

20 Claims, 9 Drawing Sheets

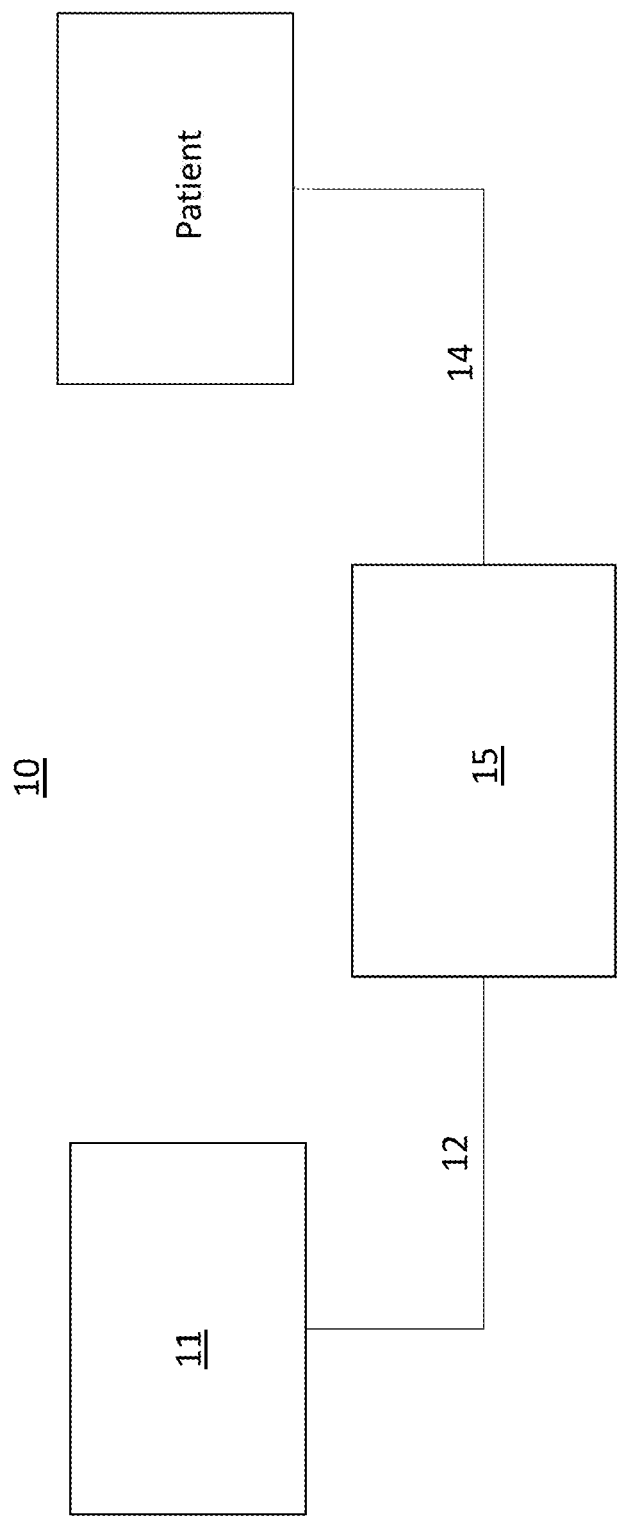

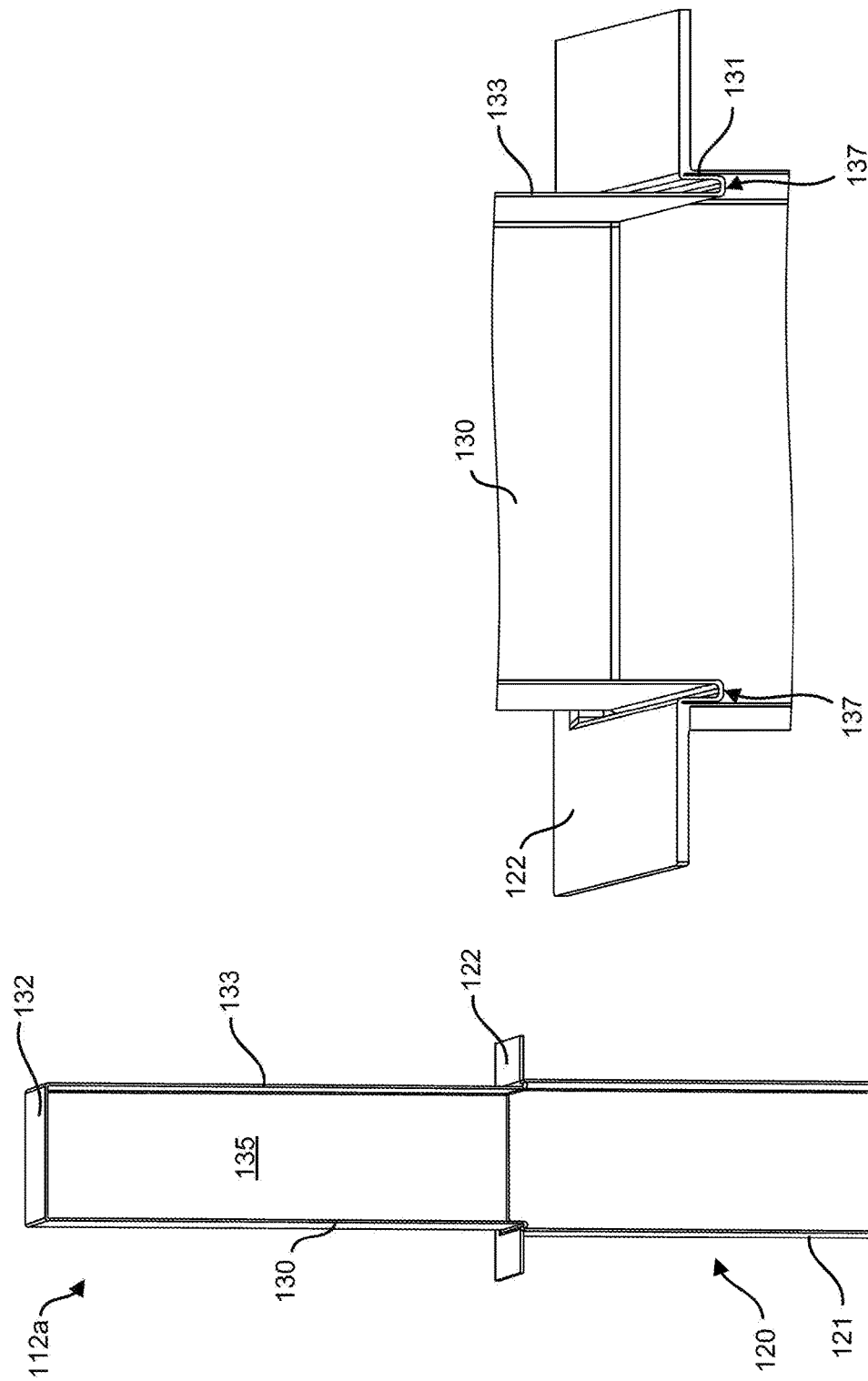

PERISTALTIC PUMP OF AN INFUSION SYSTEM FOR DELIVERY OF SMALL VOLUMES OF FLUID

TECHNICAL FIELD

The subject matter described herein relates to peristaltic pumps and peristaltic pump systems, as well as related methods.

BACKGROUND

There are a variety of applications where it is advantageous to deliver small, precise volumes of fluid. For example, the delivery of various medicaments (e.g., pain medication, insulin, etc.) are delivered from various medical devices where the delivery of such medicaments are preferably delivered in small, precise volumes to the patient. Some devices can include a peristaltic pump configured to control the delivery of the small, precise volumes. However, although peristaltic pumps can be beneficial for delivering small and precise volumes of fluids, they can be costly to manufacture and maintain. For example, peristaltic pumps can include a variety of mechanical parts, such as gears, cams, and followers that assist in the delivery of the small, precise volumes of fluids. Such mechanical parts can experience frictional forces that wear the mechanical parts down over time, which may cause the peristaltic pump to not perform as efficiently or effectively. As a result, it can be time-consuming and expensive to fix or replace the defective peristaltic pump or, alternatively, can require replacement of the entire peristaltic pump, which can also be costly. As such, there is a need for improved peristaltic pumps for the delivery of small, precise volumes of fluid.

SUMMARY

Aspects of the current subject matter can include various embodiments of a peristaltic pump and/or peristaltic pump system. In one aspect, a peristaltic pump of a medical infusion system is described that can include a housing having a fluid line passageway configured to allow a flexible tubing to extend therealong. The peristaltic pump can further include more than one tubing occluder coupled to the housing and positioned adjacent the fluid line passageway. Each of the more than one tubing occluders can have a pressure connecting end configured to communicate with a pressure source and a flexible member configured to form a collapsed configuration when a pressure within the flexible member is below a first pressure. In addition, the flexible member can form an extended configuration when the pressure within the flexible member is above a second pressure thereby causing the flexible member to extend into the fluid line passageway for pinching the flexible tubing.

In another aspect, a peristaltic pump of a medical infusion system is described that can include more than one tubing occluder. Each of the more than one tubing occluder can include a base configured to couple to a housing having a fluid line passageway for allowing a flexible tubing to extend therealong. The base can include a pressure connecting end configured to couple to a fluid line extending between the peristaltic pump and the pressure source. Each of the more than one tubing occluder can further include a flexible member configured to form a collapsed configuration when a pressure within the flexible member is below a first pressure. The flexible member can form an extended configuration when the pressure within the flexible member is above a second pressure thereby allowing the flexible member to extend into the fluid line passageway.

In some variations one or more of the following features can optionally be included in any feasible combination. The peristaltic pump can include an occluding end of the flexible member that is positioned adjacent a base of the occluder when the flexible member is in the collapsed configuration. The occluding end can be positioned a distance away from a base of the occluder when in the extended configuration. The peristaltic pump can include a first occluder of the more than one fluid line occluders that includes a first flexible member having an angled occluding end. The flexible member can be made out of a rubber material. The pressure source can be an air pump or a hydraulic pump. The more than tubing occluders can be positioned along a length of the fluid line passageway and can be configured to form the extended and collapsed configurations to cause a volume of fluid to be advanced along the flexible tubing.

In yet another aspect, a peristaltic pump system of a medical infusion system is described that can include a pressure source and a peristaltic pump having more than one tubing occluder. Each of the more than one tubing occluder can include a base configured to couple to a housing having a fluid line passageway for allowing a flexible tubing to extend therealong. The base can include a pressure connecting end configured to couple to a fluid line extending between the peristaltic pump and the pressure source. In addition, the peristaltic pump can include a flexible member configured to form a collapsed configuration when a pressure within the flexible member is below a first pressure. The flexible member can form an extended configuration when the pressure within the flexible member is above a second pressure thereby allowing the flexible member to extend into the fluid line passageway.

In some variations one or more of the following features can optionally be included in any feasible combination. The peristaltic pump system can include a valve body positioned along the fluid line for controlling the delivery of pressurized fluid to one or more of the more than one tubing occluders. The pressure source can be an air pump or a hydraulic pump. The valve body can include more than one valve, and each of the more than one valves can be configured to control the delivery of pressurized fluid from the pressure source to a respective tubing occluder of the more than one tubing occluders.

In another interrelated aspect of the current subject matter, a method of pumping fluid through a peristaltic pump of a medical infusion system is described. The method can include increasing a pressure in a flexible member of a tubing occluder of a peristaltic pump thereby causing the flexible member to form an extended configuration and apply a force against a flexible tubing thereby pinching the flexible tubing. In addition, the method can include decreasing the pressure in the flexible member of the tubing occluder thereby causing the flexible member to form a collapsed configuration and release the force against the flexible tubing.

In some variations one or more of the following features can optionally be included in any feasible combination. The method can further include controlling a valve positioned along a fluid line extending between the peristaltic pump and a pressure source. The controlling of the valve can include allowing a pressurized fluid to flow from the pressure source to the flexible member to cause the increase in the pressure and preventing the pressurized fluid flow from the pressure source to the flexible member to cause the decrease in the pressure.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings, FIG. 1A is a schematic view of an infusion system according to one implementation.

FIG. 4A is a perspective view of the first tubing occluder of the peristaltic pump of FIG. 3A showing the flexible member in an extended configuration.

FIG. 4B is a partial view of the first tubing occluder of FIG. 4A showing the occluding end of the flexible member positioned a distance from the proximal end of the base of the first tubing occluder.

When practical, similar reference numbers denote similar structures, features, or elements.

DETAILED DESCRIPTION

Figure 1B:
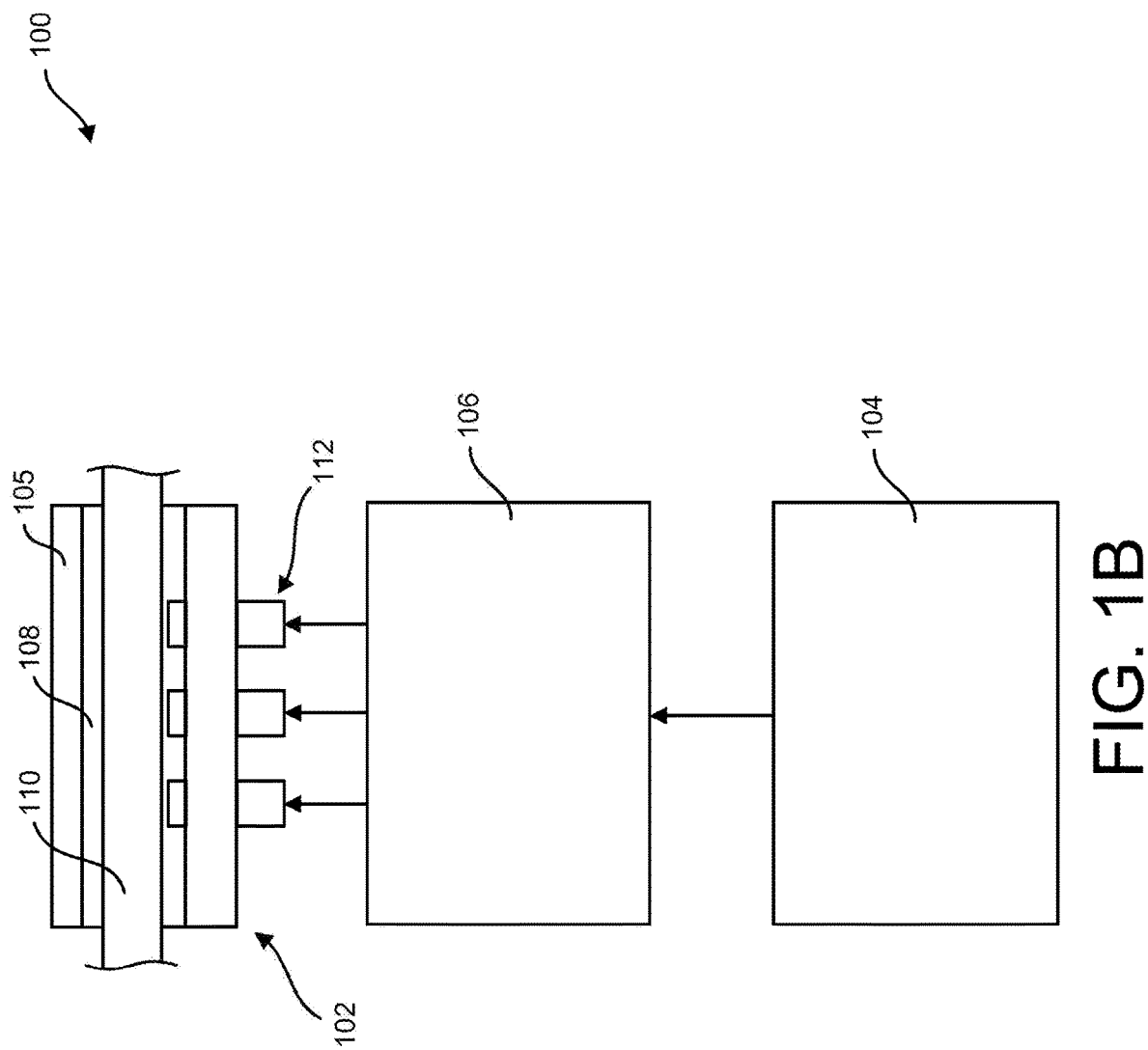
FIG. 1B is a schematic view of an embodiment of a peristaltic pump system including a peristaltic pump in fluid communication with a pressure source.

Described herein are medical fluid infusion systems including a pump system configured to deliver a fluid drug to a patient. The pump system includes a compact and modular fluid controlled peristaltic pump that is configured to advance small, precise volumes of fluid along a fluid line, such as for delivery to the patient.

FIG. 1A shows a schematic representation of a fluid infusion system 10. The fluid infusion system 10 is described herein in the context of being a bedside fluid drug infusion system for a patient although it should be appreciated that the features described herein may be used with any of a variety of fluid pumping systems and are not limited to drug infusion systems. In addition, the pump system described herein can be used for non-infusion devices.

With reference to FIG. 1A, the infusion system 10 includes a fluid container, such as an intravenous (IV) bag 11, fluidly coupled to a patient via one or more fluid conduits, such as tubes 12 and 14. A pump device 15, such as a peristaltic pump, may drive fluid from the IV bag 11 toward the patient. The IV bag 11 contains a supply of fluid (such as a liquid drug or any other fluid) to be pumped to a patient. The pump device 15 is configured to pump fluid from the IV bag 11 toward a patient via a tube 14. In an embodiment, the pump device 15 includes a disposable IV set that removably couples with the pump device, such as the Alaris® System from Becton Dickinson (San Diego, Calif.).

With reference still to FIG. 1A, the tube 12 has a proximal end fluidly coupled to the IV bag 11, such as via the drip chamber. A distal end of the tube 12 is fluidly coupled to the pump device 15. Likewise, the tube 14 has a proximal end fluidly coupled to a fluid lumen of the pump device 15 and a distal end that attaches to the patient via an IV connection. Either of the tubes 12 or 14 may be formed of a single tube (e.g., that extends through the pump device 15) or may be formed of a series of tubes removably attached to one another, such as in an end-to-end manner using any of a variety of connectors such as Luer connectors. The tubes 12 and 14 provide a fluid pathway from the IV bag 11 toward the patient. This continuous fluid lumen may include any of a variety of components that facilitate or otherwise are used in connecting the tubes and/or pumping fluid, including, for example, valves, filters, free-flow stop valves, pressure and air detection regions or components and access connectors, etc. Any of a variety of additional components may be used, including, for example, anti-free flow devices, pressure sensing components, air detection components, etc.

Various embodiments of a peristaltic pump having more than one tubing occluder that can be positioned adjacent a fluid passageway are disclosed herein. The fluid passageway can be configured to allow a flexible fluid line to extend therealong and the peristaltic pump can be configured to control advancing of small, precise volumes of fluid along from the fluid line, such as for dispensing the small, precise volumes of fluid to a patient. In some embodiments, the peristaltic pump can include a plurality of tubing occluders that each include a flexible member configured to form collapsed and extended configurations depending upon a pressure provided within the flexible member. For example, when the pressure is increased within the flexible member, the flexible member can form an extended configuration. When in the extended configuration, the flexible member can extend approximately perpendicular to the fluid pathway such that the flexible member can pinch the fluid line at a location adjacent the flexible member. When the fluid line is pinched, an inner lumen of the fluid line can be closed thereby occluding the fluid line and preventing fluid flow at the pinched location. When in a collapsed configuration, the flexible member can be folded or collapsed into a base of the occluder thereby allowing the inner lumen of the fluid line to be open such that fluid can flow past the occluder with the collapsed flexible member.

Some embodiments of the peristaltic pump disclosed herein can include more than one occluder, such as three occluders that can each be caused to form extended and collapsed configurations in at least one sequence to cause small, precise volumes of fluid to be dispensed from the fluid line. In some embodiments of the peristaltic pump, at least one of the occluders can include a feature that assists with advancing fluid along the fluid line.

Some embodiments of the peristaltic pump disclosed herein can include one or more pressure coupling features that allow the peristaltic pump to be in fluid communication with a pressure source, such as a pulse width modulated (PWM) pump. For example, the pressure source can provide pressurized fluid to the peristaltic pump for causing one or more flexible members to form extended configurations. In some embodiments, the peristaltic pump can be configured to couple to one or more of a hydraulic pump and a hydroelectric pump that delivers pressurized liquid or air, respectively, to the peristaltic pump.

Embodiments of the peristaltic pump disclosed herein can be included in a peristaltic pump system that includes at least one peristaltic pump, pressure source, and a valve body. The valve body can include one or more valves configured to control the delivery of pressurized fluid (e.g., air, liquid) from the pressure source to the peristaltic pump. For example, the valve body can control the delivery of pressure to one or more occluders to cause associated flexible members to form extended configurations. As will be described in greater detail below, the valve body can control which occluders form extended and collapsed configurations to thereby control the delivery of small, precise volumes of fluid from the fluid line. The valve body can include any number of valves that can control the passage of pressurized fluid between a pressure source and embodiments of the peristaltic pump described herein. The valve body can be controlled mechanically and/or by any number of computer processing systems, such as a processing system that can control the valve body to deliver pressurized fluid to the occluders in one or more sequences.

Some embodiments of the peristaltic pump can include a housing having a fluid passageway configured to allow a flexible tubing or flexible fluid line to extend therealong. The housing can be part of the peristaltic pump or can be part of a device to which the peristaltic pump is coupled to. As such, in some embodiments, the peristaltic pump can include a housing that can be coupled to a device. In some embodiments, the peristaltic pump can include occluders that can be directly coupled to coupling features of a device. One advantage of the peristaltic pump embodiments described herein includes the modularity and ease of replacement and repair of the peristaltic pumps. For example, the occluders of the peristaltic pumps described herein can be easily coupled to and uncoupled from the housing and/or device. This can allow a user to efficiently and cost-effectively replace one or more occluders, such as an occluder that has become damaged. In some embodiments, the housing of the peristaltic pump can be releasably coupled to the device such that the entire peristaltic pump can be efficiently and cost-effectively replaced due, in part, to the compact and simplistic design of the peristaltic pump.

Embodiments of the peristaltic pump described herein include a number of improvements and benefits over the prior art. For example, the peristaltic pumps described herein do not include mechanical parts such as cams that can wear out over time and are expensive to repair/replace. Instead, the peristaltic pumps described herein include occluders with flexible members that can require less maintenance or replacement, as well as can be efficiently and cost-effectively replaced. The pressure source and/or valve body may also be replaced in a modular fashion. Various other improvements and benefits of the peristaltic pump embodiments disclosed herein are included in the scope of this disclosure.

FIG. 1B illustrates an embodiment of a peristaltic pump system 100 including a peristaltic pump 102 in communication with a pressure source 104. As shown in FIG. 1, the peristaltic pump system 100 can include a valve body 106 positioned between the peristaltic pump 102 and pressure source 104 to control delivery of pressurized fluid (e.g., liquid, air) from the pressure source 104 to the peristaltic pump 102. The peristaltic pump 102 can include a plurality of tubing occluders 112 in communication with the pressure source 104 via the valve body 106. As will be described in greater detail below, controlled delivery of pressurized fluid from the pressure source 104 to one or more of the occluders 112 (via the valve body 106) can cause the pressurized occluder(s) 112 to transition from a collapsed configuration to an extended configuration.

As shown in FIG. 1B, the peristaltic pump 102 can include a housing 105 having a fluid passageway 108 configured to allow a flexible fluid line 110 to extend therealong. The housing 105 can be a part of a device to which the peristaltic pump 102 is coupled to or the housing 105 can be configured to be releasably coupled to the device. The device can include any number of devices configured for delivering small, precise volumes of fluid, such as a device for delivering small, precise volumes of a medicament to a patient.

Figure 2:
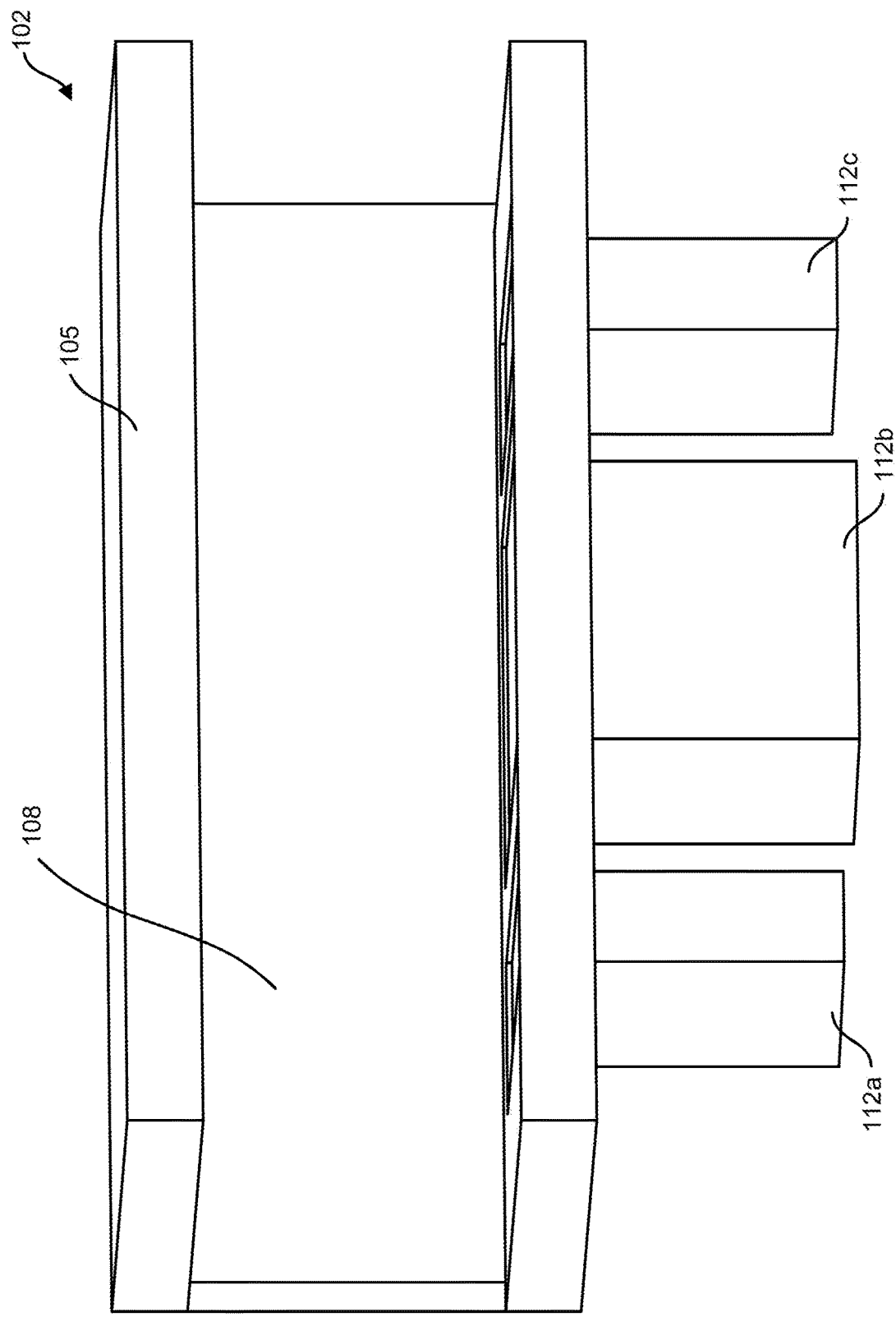
FIG. 2 is a perspective view of the peristaltic pump of FIG. 1 showing tubing occluders of the peristaltic pump positioned adjacent a fluid passageway.

FIG. 2 illustrates the peristaltic pump 100 with the plurality of occluders 112 in a collapsed configuration. As shown in FIG. 2 the plurality of occluders 112 can include a first occluder 112a, a second occluder 112b, and a third occluder 112c, with the first occluder 112a being furthest upstream relative to the direction of fluid flow passing through the peristaltic pump 100. For example, when all of the occluders 112 are in the collapsed configuration, an inner lumen of the flexible tubing 110 extending along the fluid passageway 108 is not pinched such that fluid is allowed to free-flow past the plurality of occluders 112. As will be described in greater detail below, sequencing the formation of extended and collapsed configurations between the plurality of occluders 112 can assist the peristaltic pump 102 with delivering small, precise volumes of fluid.

Figure 3B:
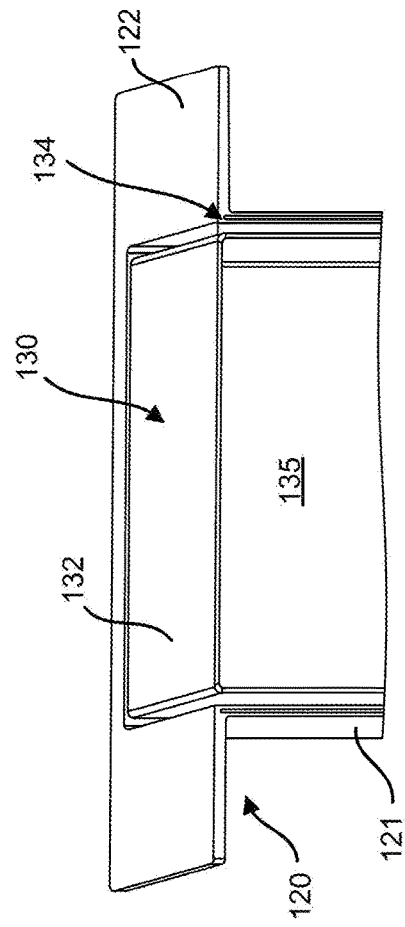
FIG. 3B is a partial cross-section view of the first tubing occluder of FIG. 3A showing an occluding end of the flexible member positioned adjacent a proximal end of a base of the first tubing occluder.
Figure 3C:
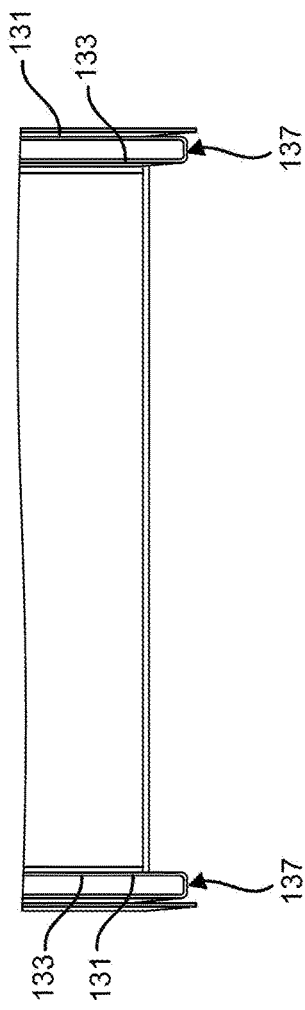
FIG. 3C is a partial cross-section view of the first tubing occluder of FIG. 3A showing a folded portion of the flexible member.
Figure 3A:
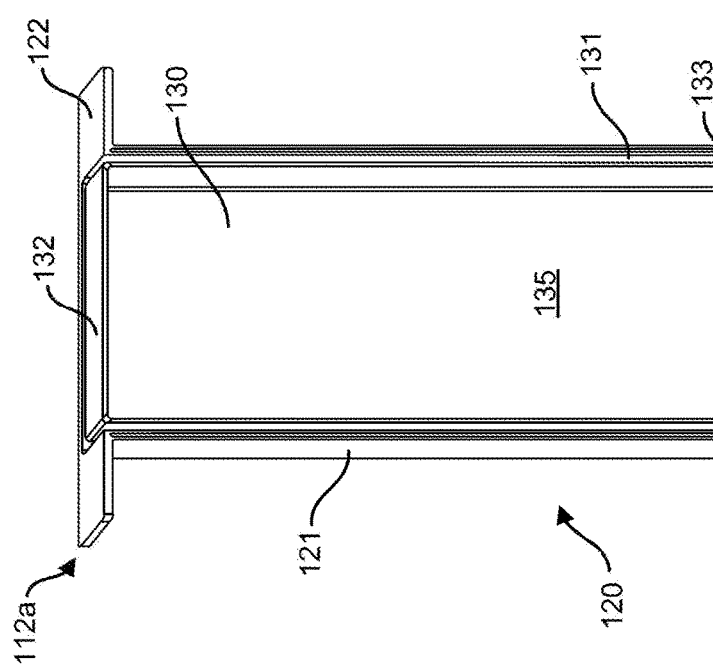
FIG. 3A is a cross-section perspective view of a first tubing occluder of the peristaltic pump of FIG. 1 showing a flexible member of the first tubing occluder in a collapsed configuration.

FIG. 3A shows a cross-section view of the first tubing occluder 112a of the peristaltic pump 102 in a collapsed configuration. As shown in FIG. 3A the first tubing occluder 112a can include a base 120 having an elongated hollow body 121 with a flange 122 at a proximal end for assisting with coupling and positioning the first tubing occluder 112a to the housing 105. The base 120 can include a pressure coupling feature 124 at a distal end that is configured to couple a pressure line for providing fluid communication between the pressure source 104 (via the valve body 106) and the first tubing occluder 112a. For example, the pressure coupling feature 124 can include threads, a quick-connect feature, or provide a sliding/friction fit for the pressure line to couple thereto. The base 120 can be rigid and/or flexible and can be made out of a variety of materials, including various types of rubber.

As shown in FIGS. 3A-3C, the first occluder 112a can include a flexible member 130 made out a flexible material. The flexible member 130 can include an occluding end 132 and a base end 134 that connects the flexible member 130 to the base 120. In some embodiments, as shown in FIG. 3B, the base end 134 of the flexible member 130 can be connected to the base 120 at or adjacent the flange 122. The flexible member 130 can include an inner chamber 135 that is in fluid communication with at least the distal end of the body 121. This can allow pressurized fluid delivered from the pressure source 104 to be directed into the inner chamber 135 of the flexible member 130. The materials of the flexible member 130 and body 121, as well as the connection between the flexible member 130 and base 120, are such that pressurized fluid directed into the inner chamber 135 can cause the flexible member to deform, including stretch in one or more directions, from a collapsed configuration to an extended configuration.

For example, the flexible member 130 can be molded such that it includes a shape-memory of the collapsed configuration and thus returns to the collapsed configuration when pressure within the inner chamber 135 is at or below a first pressure level (e.g., atmospheric pressure). As pressure is increased in the inner chamber 135 (e.g., above a second pressure level), the pressure forces can overcome the spring memory molded into the flexible member 130 thereby causing the flexible member 130 to form the extended configuration. As such, when the pressure is reduced in the inner chamber 135, the spring memory can cause the flexible member 130 to deform back to the collapsed configuration. Additionally, releasing the fluid retained in the inner chamber 135 to atmosphere (e.g., if the fluid is air) or to a reservoir (e.g., if the fluid is a liquid) can assist the flexible member 130 with transitioning from the extended configuration to the collapsed configuration. Such release of the fluid causes the pressure within the inner chamber 135 to reduce (e.g., below the first pressure level) thereby allowing the flexible member 130 to form the collapsed configuration.

As show in FIG. 3A, when the first tubing occluder 112a is in the collapsed configuration, the flexible member 130 can be folded into the base 134 such that the occluding end 132 of the flexible member 130 is positioned adjacent the flange 122, as shown in FIG. 3B. Additionally, in the collapsed configuration, a first length 131 of the flexible member 130 can extend down from the flange 122 along an inner wall of the body 121 to a folded portion 137 of the flexible member 130, as shown in FIG. 3C. The folded portion 137 can allow a second length 133 of the flexible member 130 to extend up along the first length 131 of the flexible member 130. As such, in the collapsed configuration, the occluding end 132 of the flexible member 130 can be positioned at or adjacent the proximal end of the base such that flexible member 130 does not pinch an adjacent fluid line. As shown in FIG. 3A, when the flexible member 130 is in the collapsed configuration, the first length 131 and the second length 133 of the flexible member 130 are approximately the same in length.

FIG. 4A illustrates an embodiment of the first occluder 112a in an extended configuration where the flexible member extends away from the base and the occluding end 132 is positioned a distance away from the base 120. In the extended configuration, the flexible member 130 can cause pinching of an adjacent fluid line, as will be discussed in greater detail below. As shown in FIG. 4B, when the flexible member 130 is in the extended configuration, the first length 131 can be significantly shorter than the second length 133 of the flexible member 130 and the folded portion 137 can be positioned adjacent the proximal end of the base 120.

The flexible member 130 can be made out of one or more of a variety of flexible materials and can include a variety of shapes and profiles. For example, the flexible member can have a circular, square, and/or rectangular shape or profile. Furthermore, in some embodiments, the second and third occluders 112b, 112c can include the same or similar features as described above with respect to the first occluder 112a. In some embodiments, any one of the plurality of occluders 112 can include one or more features that are not the same or similar compared to the other occluders 112. For example, flexible members 130 of the first and third occluders 112a, 112c can be the same or similar in shape and size such that they are optimized for pinching the flexible tubing and preventing fluid flow. In some embodiments, the flexible member 130 of the second occluder 112b can be sized and/or shaped different from the flexible member 130 of the first and second occluders 112a, 112c such that the flexible member 130 of the second occluder 112b is optimized for advancing fluid along the flexible tubing 110.

In some embodiments, the flexible member 130 and the base 120 can be made out of the same material and/or formed as a single part. In some embodiments, the flexible member 130 and/or the base 120 can be made using one or more of a configurable thermoformed rubber, rotocuring, a blow molding process, and an injection molding process.

As discussed above, the valve body 106 can be controlled to allow the delivery of pressurized fluid from the pressure source 104 to one or more (or none) of the flexible members 130 of the peristaltic pump 102. For example, the valve body 106 can be controlled to deliver a pressurized fluid to the first, second, and/or third occluders 112a, 112b, and/or 112c in a predetermined sequence. The predetermined sequence can cause the peristaltic pump 102 to advance a small, precise volume of liquid along the fluid line 110, such as for dispensing out of the fluid line 110. The following provides an example pumping sequence that includes the control of pressurized fluid delivery to the occluders 112 of the peristaltic pump for advancing a small, precise volume of liquid along the fluid line 110. Other sequences of pressurized fluid delivery to the occluders 112 are within the scope of this disclosure.

Figure 5:
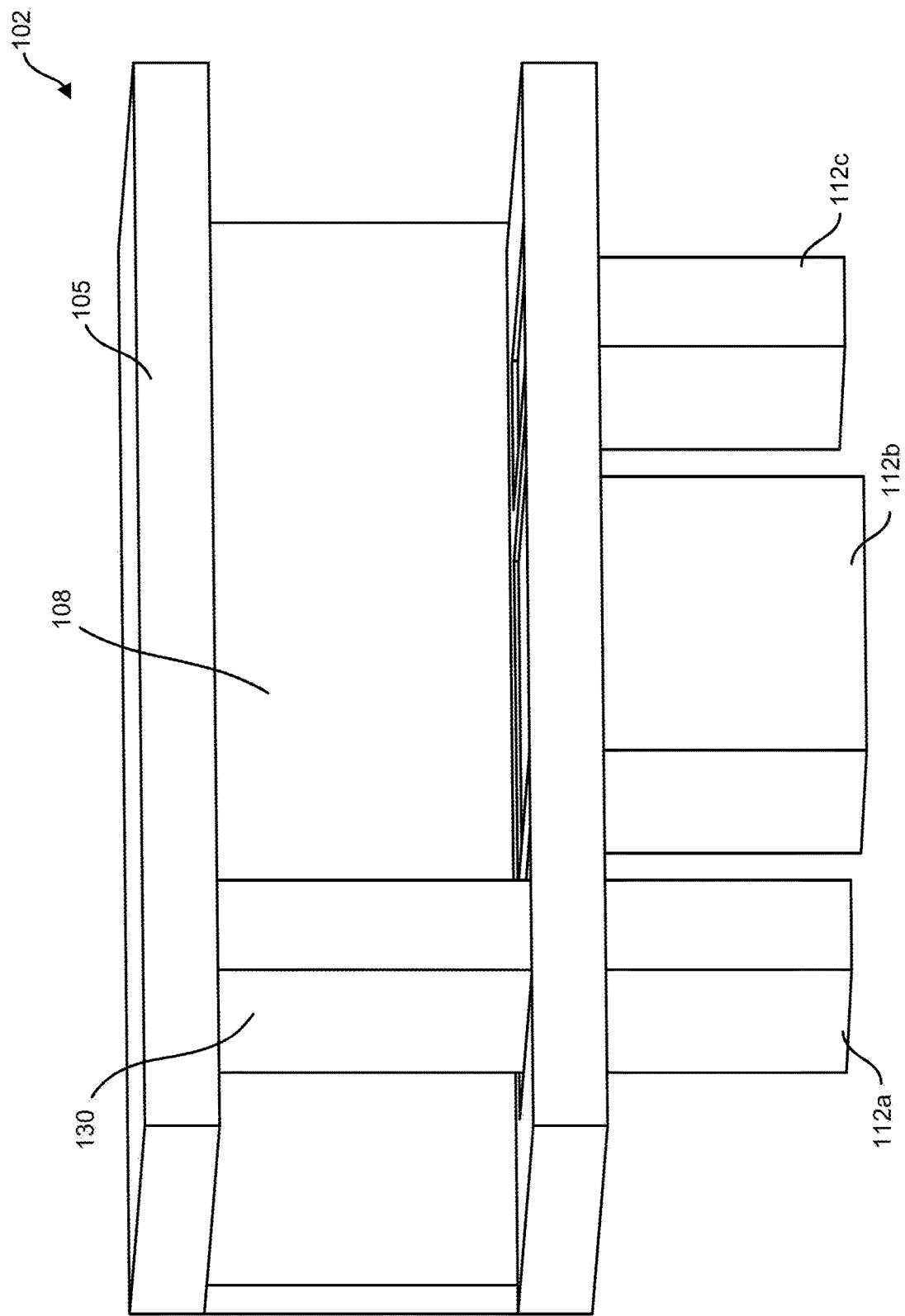
FIG. 5 is a perspective view of the peristaltic pump of FIG. 1 showing a flexible member of a first tubing occluder in an extended configuration.

FIG. 5 illustrates the peristaltic pump 102 in an example first position of the pumping sequence where pressurized fluid from the pressure source 104 is provided (via the valve body 106) to the inner chamber 135 of the flexible member 130 of the first occluder 112a, thereby allowing the flexible member to form an extended configuration. As shown in FIG. 5, in the extended configuration the flexible member 130 can extend approximately perpendicular to the fluid passageway 108. This can allow the flexible member 130 to pinch the flexible fluid line 110 extending along the fluid passageway 108. For example, the occluding end of the flexible member can apply a force against the fluid line to cause the fluid line 110 to pinch between the occluding end 132 and a side of the fluid passageway 108. As such, the flexible member 130 of the first occluder 112a can prevent fluid flow at the pinched location thus preventing free-flow along the fluid line.

Figure 6:
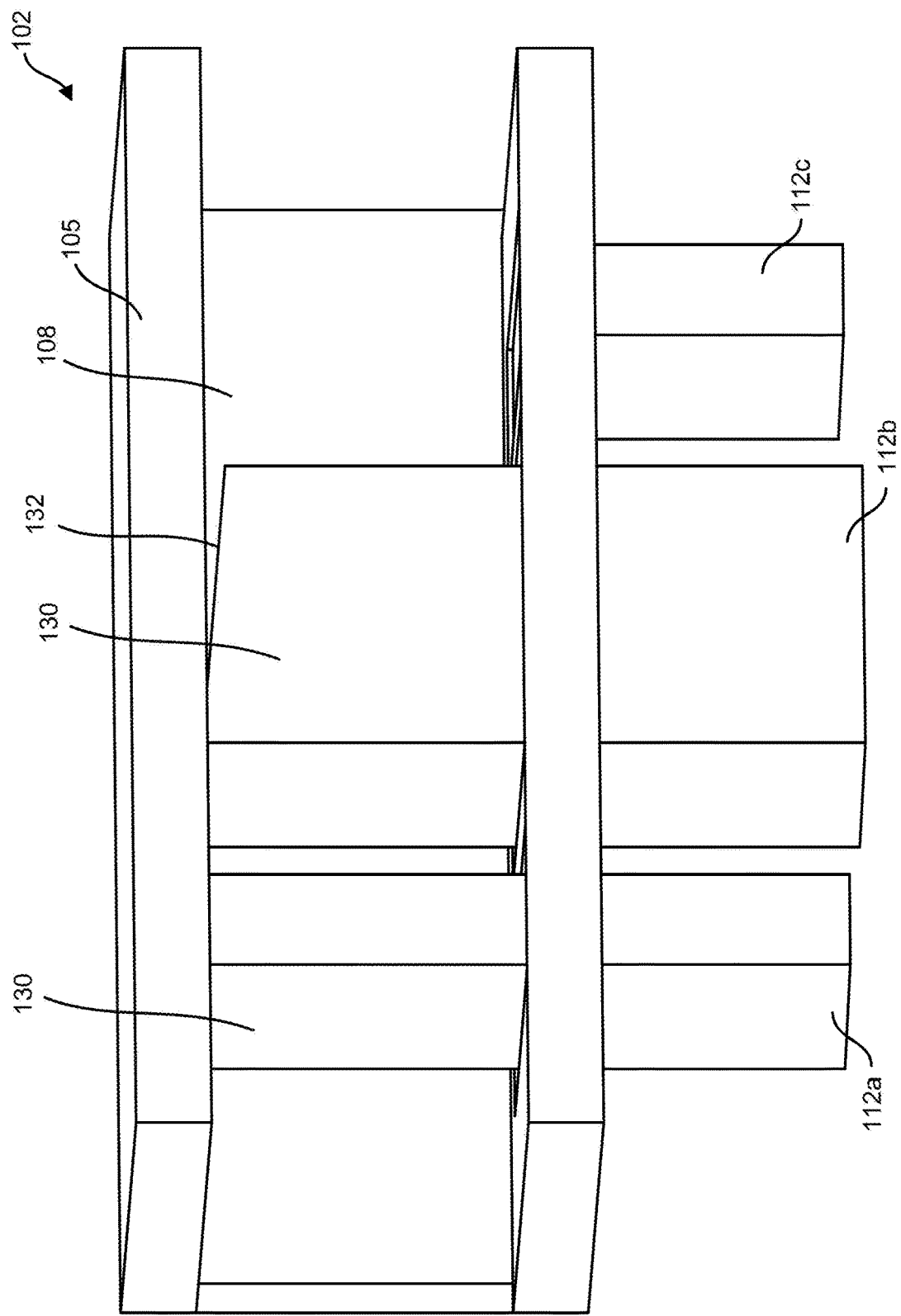
FIG. 6 is a perspective view of the peristaltic pump of FIG. 1 showing flexible members of first and second tubing occluders in extended configurations.

FIG. 6 illustrates the peristaltic pump 102 in an example second position of the pumping sequence where pressurized fluid from the pressure source 104 is provided (via the valve body 106) to the inner chambers 135 of the flexible members 130 of the first and second occluders 112a, 112b, thereby allowing such flexible members 130 to form extended configurations. As shown in FIG. 6, the second occluder 112b includes an occluding end 132 of the flexible member 130 that is angled relative to a longitudinal axis of the body of the occluder and/or the fluid line 110. The angled occluding end can assist with advancing fluid in the fluid line. For example, as shown in FIG. 6, the angled occluding end can be angled such that as the associated flexible member forms the extended configuration, the fluid line can experience a gradual closing of the inner lumen along the length of the occluding end, with the gradual closing occurring in the direction of fluid flow. As such, as the second occluder pinches the fluid line, fluid positioned along the fluid line adjacent the second occluder can be caused to advance past at least the second occluder in the direction of fluid flow.

In some embodiments, the occluding ends 132 of the flexible members 130 of the first and third occluders 112a, 112c can be parallel relative to the longitudinal axis of the fluid passageway 108 and/or perpendicular to the longitudinal axis of the body of the associated occluder body. Other shapes and profiles of the occluding end 132 of the flexible member 130 are within the scope of this disclosure.

Figure 7:
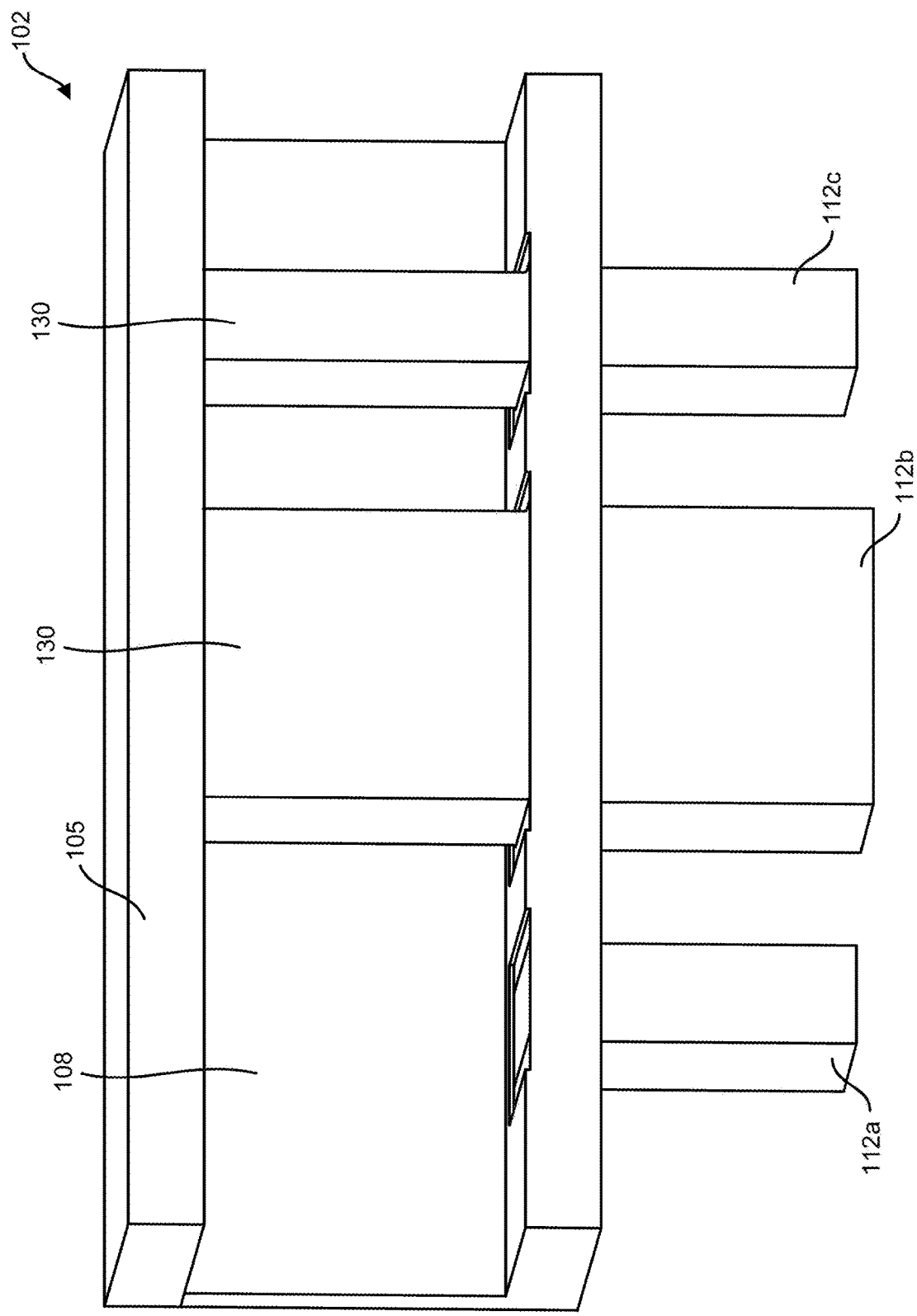
FIG. 7 is a perspective view of the peristaltic pump of FIG. 1 showing flexible members of second and third tubing occluders in extended configurations.

FIG. 7 illustrates the peristaltic pump 102 in an example third position of the pumping sequence where pressurized fluid from the pressure source is provided (via the valve body 106) to the inner chambers 135 of the flexible members 130 of the second and third occluders 112b, 112c, thereby allowing the flexible members to form extended configurations. For example, in the third position of the pumping sequence, fluid can be prevented from advancing past the second and third occluders thereby preventing free-flow of fluid along the fluid line.

Figure 8:
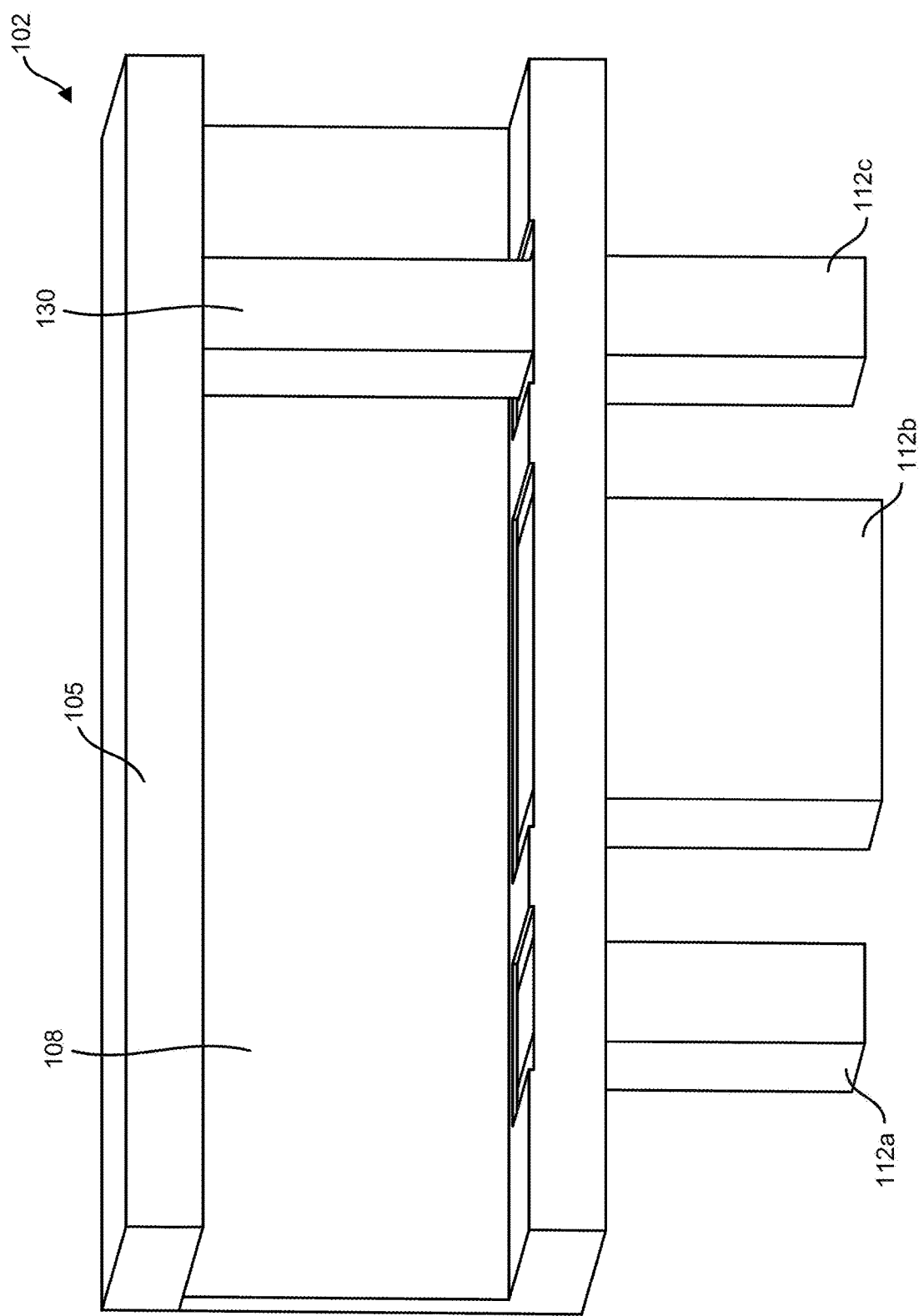
FIG. 8 illustrates a perspective view of the peristaltic pump of FIG. 1 showing the flexible member of the third tubing occluder in the extended configuration.

FIG. 8 illustrates the peristaltic pump 102 in an example fourth position of the pumping sequence where pressurized fluid from the pressure source is provided (via the valve body 106) to the inner chamber 135 of the flexible member 130 of the third occluder 112c, thereby allowing the flexible member of the third occluder to form (or maintain in) the extended configuration. For example, in the fourth position of the pumping sequence, fluid can be allowed to advance up to but not past the flexible member 130 of the third occluder 112c. The pumping sequence can then be started again to thereby advance fluid positioned along the fluid line adjacent the second occluder 112b, as described above.

In the descriptions above and in the claims, phrases such as "at least one of or" one or more of may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. A peristaltic pump of a medical infusion system, comprising:
    a housing having a fluid line passageway configured to allow a flexible tubing to extend therealong; and
    more than one tubing occluder coupled to the housing and positioned adjacent the fluid line passageway, each of the more than one tubing occluders comprising:
        a base comprising an elongated hollow body with a first end that couples to the housing, the base having a pressure connecting end configured to communicate with a pressure source; and
        a flexible member coupled to the first end of the base, the flexible member being configured to form a collapsed configuration when a pressure within the flexible member is below a first pressure thereby causing the flexible member to collapse into the elongated hollow body of the base, the flexible member forming an extended configuration when the pressure within the flexible member is above a second pressure thereby causing the flexible member to extend out of the elongated hollow body of the base and into the fluid line passageway for pinching the flexible tubing, the flexible member including a folded portion that moves along a length of the base to allow the flexible member to move between the collapsed configuration and the extended configuration, the folded portion being advanced toward the pressure connecting end as the flexible member moves into the collapsed configuration and the folded portion being advanced toward the fluid line passageway as the flexible member moves into the extended configuration.

2. The peristaltic pump of claim 1, wherein the flexible member comprises an occluding end positioned adjacent the first end of the base when the flexible member is in the collapsed configuration.

3. The peristaltic pump of claim 2, wherein the occluding end applies a force against the flexible tubing when the flexible member is in the extended configuration.

4. The peristaltic pump of claim 1, wherein a first occluding end of a first tubing occluder of the more than one tubing occluders includes an angled surface that increases contact with the flexible tubing as the respective flexible member moves into the extended configuration to force a volume of fluid to advance along the flexible tubing.

5. The peristaltic pump of claim 1, wherein the flexible member is made out of a rubber material.

6. The peristaltic pump of claim 1, wherein the pressure source is an air pump or a hydraulic pump.

7. The peristaltic pump of claim 1, wherein the more than one tubing occluders are positioned along a length of the fluid line passageway and are configured to form the extended and collapsed configurations to cause a volume of fluid to be advanced along the flexible tubing.

8. A peristaltic pump system of a medical infusion system, comprising:
    a pressure source; and
    a peristaltic pump having more than one tubing occluder, each of the more than one tubing occluders including:
        a base comprising an elongated hollow body with a first end configured to couple to a housing having a fluid line passageway for allowing a flexible tubing to extend therealong, the base including a pressure connecting end configured to couple to a fluid line extending between the peristaltic pump and the pressure source; and a flexible member coupled to the first end of the base, the flexible member being configured to form a collapsed configuration when a pressure within the flexible member is below a first pressure thereby causing the flexible member to collapse into the elongated hollow body of the base, the flexible member forming an extended configuration when the pressure within the flexible member is above a second pressure thereby allowing the flexible member to extend out of the elongated hollow body of the base and into the fluid line passageway, the flexible member including a folded portion that moves along a length of the base to allow the flexible member to move between the collapsed configuration and the extended configuration, the folded portion being advanced toward the pressure connecting end as the flexible member moves into the collapsed configuration and the folded portion being advanced toward the fluid line passageway as the flexible member moves into the extended configuration.

9. The peristaltic pump system of claim 8, further comprising a valve body positioned along the fluid line for controlling a delivery of pressurized fluid to one or more of the more than one tubing occluders.

10. The peristaltic pump system of claim 9, wherein the valve body includes more than one valve, and each of the more than one valves being configured to control the delivery of pressurized fluid from the pressure source to a respective tubing occluder of the more than one tubing occluders.

11. The peristaltic pump system of claim 8, wherein the pressure source is an air pump or a hydraulic pump.

12. A method of pumping fluid through a peristaltic pump of a medical infusion system, comprising:

increasing a pressure in a flexible member of a tubing occluder of a peristaltic pump thereby causing the flexible member to form an extended configuration and apply a force against a flexible tubing thereby pinching the flexible tubing, the flexible member being coupled to a first end of a base of the tubing occluder, the base comprising an elongated hollow body with a pressure connecting end configured to communicate with a pressure source, the flexible member extending out of the elongated hollow body of the base to form the extended configuration; and decreasing the pressure in the flexible member of the tubing occluder thereby causing the flexible member to collapse into the elongated hollow body of the base and form a collapsed configuration, the collapsed configuration of the flexible tubing causing the force against the flexible tubing to be released, the flexible member including a folded portion that moves along a length of the base to allow the flexible member to move between the collapsed configuration and the extended configuration, the folded portion being advanced toward the pressure connecting end of the base as the flexible member moves into the collapsed configuration and the folded portion being advanced away from the pressure connecting end as the flexible member moves into the extended configuration.

13. The method of claim 12, further comprising:

controlling a valve positioned along a fluid line extending between the peristaltic pump and a pressure source, the controlling including allowing a pressurized fluid to flow from the pressure source to the flexible member to cause the increase in the pressure and preventing the pressurized fluid flow from the pressure source to the flexible member to cause the decrease in the pressure.

14. A peristaltic pump of a medical infusion system, comprising:

more than one tubing occluder, each of the more than one tubing occluder including:

a base having an elongated hollow body with a first end that couples to a housing of the peristaltic pump, the housing having a fluid line passageway for allowing a flexible tubing to extend therealong, the base including a pressure connecting end configured to couple to a fluid line extending between the peristaltic pump and a pressure source; and a flexible member coupled to the first end of the base, the flexible member being configured to form a collapsed configuration when a pressure within the flexible member is below a first pressure thereby causing the flexible member to collapse into the elongated hollow body of the base, the flexible member forming an extended configuration when the pressure within the flexible member is above a second pressure thereby allowing the flexible member to extend out of the elongated hollow body of the base and into the fluid line passageway, the flexible member including a folded portion that moves along a length of the base to allow the flexible member to move between the collapsed configuration and the extended configuration, the folded portion being advanced toward the pressure connecting end as the flexible member moves into the collapsed configuration and the folded portion being advanced toward the fluid line passageway as the flexible member moves into the extended configuration.

15. The peristaltic pump of claim 14, wherein the flexible member comprises an occluding end positioned adjacent the first end of the base when the flexible member is in the collapsed configuration.

16. The peristaltic pump of claim 15, wherein the occluding end applies a force against the flexible tubing when the flexible member is in the extended configuration.

17. The peristaltic pump of claim 14, wherein a first occluding end of a first tubing occluder of the more than one tubing occluders includes an angled surface that increases contact with the flexible tubing as the respective flexible member moves into the extended configuration to force a volume of fluid to advance along the flexible tubing.

18. The peristaltic pump of claim 14, wherein the flexible member is made out of a rubber material.

19. The peristaltic pump of claim 14, wherein the pressure source is an air pump or a hydraulic pump.

20. The peristaltic pump of claim 14, wherein the more than one tubing occluders are positioned along a length of the fluid line passageway and are configured to form the extended and collapsed configurations to cause a volume of fluid to be advanced along the flexible tubing.

* * * * *